United States Patent
Xu et al.

(10) Patent No.: US 9,708,389 B2
(45) Date of Patent: Jul. 18, 2017

(54) METHOD FOR PREPARING HOMODIMER PROTEIN MIXTURE BY USING CHARGE REPULSION EFFECT

(71) Applicant: SUZHOU ALPHAMAB CO., LTD, Suzhou (CN)

(72) Inventors: Ting Xu, Suzhou (CN); Tao Xu, Suzhou (CN); Xiaoxiao Wang, Suzhou (CN); Xinglu Sun, Suzhou (CN); Ying Fan, Suzhou (CN); Yan Zeng, Suzhou (CN)

(73) Assignee: Suzhou Alphamab Co., Ltd., Suzhou, Jiangsu (CN)

( * ) Notice: Subject to any disclaimer, the term of this patent is extended or adjusted under 35 U.S.C. 154(b) by 160 days.

(21) Appl. No.: 14/416,817

(22) PCT Filed: Jul. 25, 2013

(86) PCT No.: PCT/CN2013/080060
§ 371 (c)(1),
(2) Date: May 7, 2015

(87) PCT Pub. No.: WO2014/015804
PCT Pub. Date: Jan. 30, 2014

(65) Prior Publication Data
US 2015/0274807 A1    Oct. 1, 2015

(30) Foreign Application Priority Data
Jul. 25, 2012 (CN) .......................... 2012 1 0258592

(51) Int. Cl.
| A61K 39/00 | (2006.01) |
| C07K 16/00 | (2006.01) |
| C12P 21/02 | (2006.01) |
| A61K 39/395 | (2006.01) |

(52) U.S. Cl.
CPC ............ *C07K 16/00* (2013.01); *A61K 39/395* (2013.01); *C12P 21/02* (2013.01); *C07K 2317/21* (2013.01); *C07K 2317/526* (2013.01); *C07K 2317/622* (2013.01); *C07K 2317/64* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| 5,789,208 A | 8/1998 | Sharon |
| 6,335,163 B1 | 1/2002 | Sharon |
| 2005/0170398 A1 | 8/2005 | Van Berkel et al. |
| 2009/0182127 A1* | 7/2009 | Kjaergaard ........ C07K 16/2803 530/387.3 |
| 2010/0286374 A1* | 11/2010 | Kannan ................ C07K 16/468 530/387.3 |

FOREIGN PATENT DOCUMENTS

| CN | 102558355 | 7/2012 |
| CN | 102851338 | 1/2013 |
| EP | 1 870 459 | 12/2007 |
| WO | 2010084197 | 7/2010 |
| WO | 2011063348 | 5/2011 |

OTHER PUBLICATIONS

Lee et al. (Molecular and Cellular Biology, 2010, 30:2621-2635).*
M. J. Nohaile et al., "Altering dimerization specificity by changes in surface electrostatics", PNAS, 98(6):3109-3114, 2001.
Kazumasa Sakurai and Yuji Goto, "Manipulating Monomer-Dimer Equilibrium of Bovine β-Lactoglobulin by Amino Acid Substitution", The Journal of Biological Chemistry, 277(28):25735-25740, 2002.
PCT/CN2013/080060 International Search Report dated Oct. 31, 2013.
Kannan Gunasekaran, Enhancing Antibody Fc Heterodimer Formation through Electrostatic Steering Effects, The Journal of Biological Chemistry, Jun. 18, 2010, pp. 19637-19646, vol. 285, No. 25, The American Society for Biochemistry and Molecular Biology, Inc., USA.

* cited by examiner

*Primary Examiner* — Julie Wu
(74) *Attorney, Agent, or Firm* — Honigman Miller Schwartz and Cohn LLP; Thomas A. Wootton; Jonathan P. O'Brien

(57) ABSTRACT

The invention relates to a method for preparing a homodimer protein mixture by using repulsive interaction of charges. The method comprises the step of replacing part of residues with the opposite-charged residues, so that different proteins or antibodies are unfavorable to forming heterodimers due to the repulsive interaction between like charges, while same proteins or antibodies are favorable to forming homodimers due to attractive interaction between opposite charges. The homodimer protein mixture obtained according to the method of the invention can simultaneously act on different epitopes of the same target, and simultaneously inhibit the effects of a plurality of antigens by binding to the antigens from different sources, thereby providing a new approach towards immunological diagnosis and treatment of tumors and other diseases.

20 Claims, 6 Drawing Sheets

(a)

```
                      340       350       360       370       380       390
                       |         |         |         |         |         |
IGG1_HUMAN   AKGQPREPQVYTLPPSRDELTKNQVSLTCLVKGFYPSDIAVEWESNGQPENNYKTTPPVL
IGG2_HUMAN   TKGQPREPQVYTLPPSREEMTKNQVSLTCLVKGFYPSDIAVEWESNGQPENNYKTTPPML
IGG3_HUMAN   TKGQPREPQVYTLPPSREEMTKNQVSLTCLVKGFYPSDIAVEWESSGQPENNYNTTPPML
IGG4_HUMAN   AKGQPREPQVYTLPPSQEEMTKNQVSLTCLVKGFYPSDIAVEWESNGQPENNYKTTPPVL
                    * ***  ****  *   * * *                   *  * ** *
```

```
                      400       410       420       430       440
                       |         |         |         |         |
IGG1_HUMAN   DSDGSFFLYSKLTVDKSRWQQGNVFSCSVMHEALHNHYTQKSLSLSPGK   SEQ ID NO:5
IGG2_HUMAN   DSDGSFFLYSKLTVDKSRWQQGNVFSCSVMHEALHNHYTQKSLSLSPGK   SEQ ID NO:6
IGG3_HUMAN   DSDGSFFLYSKLTVDKSRWQQGNIFSCSVMHEALHNRFTQKSLSLSPGK   SEQ ID NO:7
IGG4_HUMAN   DSDGSFFLYSRLTVDKSRWQEGNVFSCSVMHEALHNHYTQKSLSLSLGK   SEQ ID NO:8
             **    * * *
```

(b)

```
IGG1_MOUSE   TKGRPKAPQVYTIPPPKEQMAKDKVSLTCMITDFFPEDITVEWQWNGQPAENYKNTQPIM
IGG2A_MOUSE  PKGSVRAPQVYVLPPPEEEMTKKQVTLTCMVTDFMPEDIYVEWTNNGKTELNYKNTEPVL
IGG2B_MOUSE  IKGLVRAPQVYTLPPPAEQLSRKDVSLTCLVVGFNPGDISVEWTSNGHTEENYKDTAPVL
IGG3_MOUSE   PKGRAQTPQVYTIPPPREQMSKKKVSLTCLVTNFFSEAISVEWERNGELEQDYKNTPPIL
                    * ***  ****  *   * * *                   *  * ** *
```

```
IGG1_MOUSE   NTNGSYFVYSKLNVQKSNWEAGNTFTCSVLHEGLHNHHTEKSLSHS   SEQ ID NO:9
IGG2A_MOUSE  DSDGSYFMYSKLRVEKKNWVERNSYSCSVVHEGLHNHHTTKSFSRT   SEQ ID NO:10
IGG2B_MOUSE  DSDGSYFIYSKLNMKTSKWEKTDSFSCNVRHEGLKNYYLKKTISRS   SEQ ID NO:11
IGG3_MOUSE   DSDGTYFLYSKLTVDTDSNLQGEIFTCSVVHEALHNHHTQKNLSRS   SEQ ID NO:12
```

(c)

```
IGA_HUMAN    -SGNT-FRPEVHLLPPPSEELALNELVTLTCLARGFSPKDVLVRWLQGSQELPREKYLTW
IGE_HUMAN    TSGPR-AAPEVYAFATPEWPGSRDK-RTLACLIQNFMPEDISVQWLHNEVQLPDARHSTT
IGD_HUMAN    REPAA-QAPVKLSLNLLASSDPPEAASWLLCEVSGFSPPNILLMWLEDQREVNTSGFAPA
IGM_HUMAN    PKGVALHRPDVYLLPPAREQLNLRESATITCLVTGFSPADVFVQWMQRGQPLSPEKYVTS
                 * ***  ****  *   * * *                   *  * **
```

```
IGA_HUMAN    ASRQEPSQGTTTFAVTSILRVAAEDWKKGDTFSCMVGHEAL-PLAFTQKTIDRLAGK   SEQ ID NO:13
IGE_HUMAN    QPRKT---KGSGFFVFSRLEVTRAEWEQKDEFICRAVHEAASPSQTVQRAVSVNPGK   SEQ ID NO:14
IGD_HUMAN    RPPPQP--GSTTFWAWSVLRVPAPPSPQPATYTCVVSHEDSRTLLNASRSLEVSYVT   SEQ ID NO:15
IGM_HUMAN    APMPEP-QAPGRYFAHSILTVSEEEWNTGETYTCVVAHEAL-PNRVTERTVDKSTGK   SEQ ID NO:16
             * * *  *   ***                              *
```

Fig. 3

Heterodimer
(a) wild type
favor to form heterodimer
(a) D399K&&K409D
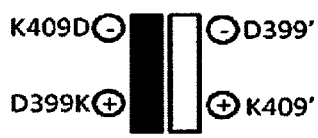
unfavor to form heterodimer
Homodimer
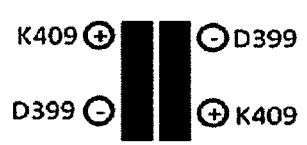 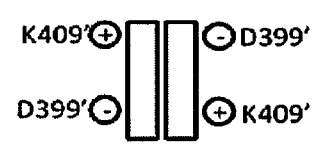
favor to form homodimer
favor to form homodimer
Fig. 4

METHOD FOR PREPARING HOMODIMER PROTEIN MIXTURE BY USING CHARGE REPULSION EFFECT

REFERENCE TO RELATED APPLICATIONS

This application claims priority to PCT application PCT/CN2013/080060, filed Jul. 25, 2013, which claims the benefit of Chinese patent application no. 201210258592.8, filed Jul. 25, 2012, the entire contents of which are incorporated herein by reference.

SEQUENCE LISTING

This application incorporates in its entirety the Sequence Listing entitled "2015-05-07_235427-368276_SE-Q_LIST_ST25" (22, 182 bytes), which was created on May 7, 2015, and filed electronically herewith.

FIELD OF THE INVENTION

The invention relates to a method for preparing a mixture of homodimer proteins, in particular to a method for preparing a mixture of homodimer proteins by using repulsive interaction of charges. The invention further relates to a homodimer protein mixture obtained by the method and uses of the method for preparing the homodimer protein mixture.

BACKGROUND OF THE INVENTION

Monoclonal antibody drugs have made significant progress in recent 15 years and have become driving force in pharmaceutical industry. Since 1996, about 30 monoclonal antibody drugs in total have been approved, wherein the annual sales for nine drugs reached over 1 billion US dollars. In 2010, the overall sales of monoclonal antibody drugs were over 30 billion US dollars and the annual rate of growth was over 10%. The monoclonal antibody only inhibits a single target due to the high specificity against the target thereof. However, it may be necessary to inhibit multiple targets/signal pathways to avoid a compensatory effect for tumors, autoimmune diseases, and other diseases. For viral infection, due to the high mutation rate of viruses, in general, it is necessary to inhibit multiple antigenic sites in order to prevent escape. There are several alternative solutions. One is to use polyclonal antibodies, or to obtain a heterodimer, e.g. a bispecific antibody, by modifying Fc fragments of antibodies. Another solution is to use an antibody mixture for treatment, wherein the antibody mixture comprises two or more antibodies against different epitopes on the same target, or against different targets.

U.S. Pat. No. 7,262,028 discloses a method for producing a bivalent antibody or a mixture of bivalent antibodies from a single host cell clone by expression of one light chain and different heavy chains, and also provides a method for producing a combination of antibodies which can be screened for the usefulness in various applications.

WO/2010/084197 describes a method for producing a mixture comprising two or more different antibodies from a single host cell clone. In one embodiment, a mixture of different monovalent antibodies is produced. In another embodiment, a mixture of monovalent and bivalent antibodies is produced. In the method, homodimers are stabilized by virtue of the natural exchange phenomenon between two Fab arms of IgG4, wherein some residues of the hinge region and CH3 domain which caused the phenomenon are changed. However, the patent does not mention whether the problem of existence of heterodimers is completely solved.

U.S. Pat. Nos. 5,789,208 and 6,335,163 described a method for expressing a library of polyclonal antibodies, wherein a library of polyclonal Fab fragments was expressed on a phage display vector, and then screened for the reactivity to antigens. The selected combinations of variable region genes of heavy chains and light chains are transferred in a linked pairing way into an eukaryotic expression vector comprising constant region genes so as to obtain a sublibrary of complete polyclonal antibodies. After the sublibrary is transfected into myeloma cells, stable clones would produce antibodies which can be mixed to obtain a mixture of monoclonal antibodies. By using the method, although it is theoretically possible to directly obtain polyclonal antibodies from one recombination production process by culturing a group of mixed transfected cells, there may be potential problems in terms of the stability of group of the mixed cells and thus the consistency of the produced polyclonal antibodies. In a pharmaceutically acceptable large-scale (industrial) production method, it is an arduous task to control different cells in a whole group. For example, the properties such as the growth rate of cells and the production rate of antibodies should be kept stable for all single clones in the non-clonal group, so that the ratio of the antibodies in the mixture of polyclonal antibodies can be kept constant. Therefore, although the production for mixed antibodies may have been realized in the art, there are still no ameanable solutions which are economically and practically sounding for large scale manufacturing.

Recently, Merck and Symphogen A/S company from Denmark signed an exclusive worldwide license agreement for Sym004. Sym004 is a novel antibody mixture which is now being developed and targets the epithelial growth factor receptor (EGFR).

Sym004 consists of two antibodies, can block ligand binding, receptor activation and downstream signaling, and is also considered to elicit removal of the EGFR receptors from the cancer cell surface by inducing EGFR internalization and degradation. Sym004 is currently being evaluated in a Phase I/II trial for the treatment of patients with advanced wild-type KRAS metastatic colorectal cancer (mCRC) who have previously progressed on treatment with standard chemotherapy and a commercially available anti-EGFR monoclonal antibody. In addition, a Phase II trial in patients with squamous cell carcinoma of the head and neck (SCCHN) who have failed anti-EGFR-based therapy is currently ongoing.

The antibody mixture technology of Symphogen A/S company involves the following: firstly obtaining a plurality of antibodies against the same target by an antibody screening platform, then performing molecular construction for each antibody, culturing cells in shake-flask, and mixing the cells, and culturing the cell mixture in a way of gradual amplification culture, then performing a optimized purification to obtain the final product. However, the method still involves the problems caused by unstable cell growth rate and antibody production rate, since recombinant host cells are used in the method for producing a mixture of various homodimers. Because a single antibody is expressed in a single cell in the method, the method does not involve the problem of heterodimers.

In all means, it would be a more ideal for producing a protein or antibody mixture, If two or more proteins or antibodies can be produced in single recombinant cell clone,

CONTENTS OF THE INVENTION

Based on a large body of experiments, the inventors developed a method for simultaneously preparing two or more proteins or antibodies from a single recombinant cell clone. The invention specifically comprises the following aspects:

The first aspect of the invention relates to a method for obtaining a mixture containing two or more proteins by using single recombinant cell clone, wherein the protein is in the form of a dimer which is formed by polymerization between monomer chains, and the two or more proteins contain the same domain, wherein the method comprises the step of replacing part of residues of the two monomer chains in the same domain of one or more proteins with the opposite-charged amino acid(s), so that the monomer chains from different proteins are unfavorable to forming heterodimers due to the repulsive interaction between like charges, while the monomer chain from the same protein is more favorable to forming homodimers due to the attractive interaction between opposite charges.

In an embodiment of the invention, the protein is an antibody or a fusion protein comprising a part of the antibodies.

The method according to any one embodiment of the first aspect of the invention, the residues of at most one protein are not replaced. In an embodiment of the invention, the residues of one protein are not replaced while the residues of the other protein are replaced. In another embodiment of the invention, the residues of the two proteins are both replaced.

When the residues of multiple (two or more) proteins are replaced, at least one position of the replaced residues among different proteins are different, preferably, all the positions of the replaced residues among different proteins are different.

The method according to any one embodiment of the first aspect of the invention, the same domain refers to CH3 domain of an antibody.

The method according to any one embodiment of the first aspect of the invention, the same domain refers to Fc region of an antibody.

The method according to any one embodiment of the first aspect of the invention, the antibodies are derived from mammals, such as human, mice or rats.

The method according to any one embodiment of the first aspect of the invention, the antibodies are selected from the group consisting of IgG (such as IgG1, IgG2, IgG3), IgA (such as IgA1, IgA2), IgE, IgD and IgM (such as IgM1, IgM2).

The method according to any one embodiment of the first aspect of the invention, replacing part of residues in the same domains with the opposite-charged residues comprises the following steps:
(1) obtaining the interface residues between the same domains of the two monomer chains of the protein;
(2) selecting paired residues with paired positive and negative charges from the interface residues obtained in step (1); and
(3) selecting one or more pairs (such as two pairs, three pairs or four pairs) of residues from the paired residues with the paired positive and negative charges obtained in step (2), and replacing residues of the selected pairs with the opposite-charged residues.

In an embodiment of the invention, the charged amino acid is selected from the group consisting of lysine (lys), arginine (Arg), histidine (His), aspartic acid (Asp) and glutamic acid (Glu).

In an embodiment of the invention, the same domain refers to the Fc region or the CH3 domain of the antibody, and the paired charged residues with the paired positive and negative charges are selected from the group consisting of the following paired residues as shown in a)-h):
a) Glu (E) at position 356 of the first chain and Lys (K) at position 439 of the second chain;
b) Glu (E) at position 357 of the first chain and Lys (K) at position 370 of the second chain;
c) Lys (K) at position 370 of the first chain and Glu (E) at position 357 of the second chain;
d) Lys (K) at position 392 of the first chain and Asp (D) at position 399 of the second chain;
e) Asp (D) at position 399 of the first chain and Lys (K) at position 392 of the second chain;
f) Asp (D) at position 399 of the first chain and Lys (K) at position 409 of the second chain;
g) Lys (K) at position 409 of the first chain and Asp (D) at position 399 of the second chain; and
h) Lys (K) at position 439 of the first chain and Glu (E) at position 356 of the second chain;
the positions of the above 8 pairs of residues are determined according to the EU numbering index of KABAT system for antibody.

In an embodiment of the invention, replacing the part of residues of the two monomer chains in the same domains of one or more proteins with the opposite-charged residues refers to one or any combination of the following situations:
(1) replacing Lys at position 392 with Asp, replacing Lys at position 409 with Asp and replacing Asp at position 399 with Lys for one protein;
(2) replacing Glu at position 356 with Lys and replacing Lys at position 439 with Glu for one protein;
(3) replacing Glu at position 357 with Lys and replacing Lys at position 370 with Glu for one protein;
(4) replacing Glu at position 357 with Lys, replacing Lys at position 370 with Glu, replacing Lys at position 392 with Asp, replacing Lys at position 409 with Asp and replacing Asp at position 399 with Lys for one protein;
(5) replacing Lys at position 392 with Asp and replacing Asp at position 399 with Lys for one protein;
(6) replacing Asp at position 399 with Lys and replacing Lys at position 409 with Asp for one protein;
(7) replacing Lys at position 392 with Asp, replacing Lys at position 409 with Asp and replacing Asp at position 399 with Lys for one protein; and simultaneously, replacing Glu at position 357 with Lys and replacing Lys at position 370 with Glu for the other protein; and
(8) replacing Lys at position 392 with Asp, replacing Lys at position 409 with Asp and replacing Asp at position 399 with Lys for one protein; and simultaneously, replacing Glu at position 356 with Lys and replacing Lys at position 439 with Glu for the other protein.

In an embodiment of the invention, the paired charged residues with the paired positive and negative charges in sequence as shown in SEQ ID NO: 2 are 8 pairs of residues as shown in a1)-h1):
a1) Glu (E) at position 161 of the first chain and Lys (K) at position 244 of the second chain;
b1) Glu (E) at position 162 of the first chain and Lys (K) at position 175 of the second chain;
c1) Lys (K) at position 175 of the first chain and Glu (E) at position 163 of the second chain;
d1) Lys (K) at position 197 of the first chain and Asp (D) at position 204 of the second chain;
e1) Asp (D) at position 204 of the first chain and Lys (K) at position 197 of the second chain;
f1) Asp (D) at position 204 of the first chain and Lys (K) at position 214 of the second chain;

g1) Lys (K) at position 214 of the first chain and Asp (D) at position 204 of the second chain;

h1) Lys (K) at position 244 of the first chain and Glu (E) at position 161 of the second chain.

In an embodiment of the invention, the paired charged residues with the paired positive and negative charges in the sequence as shown in SEQ ID NO: 4 are 8 pairs of residues as shown in a2)-h2):

a2) Glu (E) at position 399 of the first chain and Lys (K) at position 482 of the second chain;

b2) Glu (E) at position 400 of the first chain and Lys (K) at position 413 of the second chain;

c2) Lys (K) at position 413 of the first chain and Glu (E) at position 400 of the second chain;

d2) Lys (K) at position 435 of the first chain and Asp (D) at position 442 of the second chain;

e2) Asp (D) at position 442 of the first chain and Lys (K) at position 435 of the second chain;

f2) Asp (D) at position 442 of the first chain and Lys (K) at position 452 of the second chain;

g2) Lys (K) at position 452 of the first chain and Asp (D) at position 442 of the second chain;

h2) Lys (K) at position 482 of the first chain and Glu (E) at position 399 of the second chain.

The method according to any one embodiment of the first aspect of the invention, the process of replacing part of residues in the same domains with the opposite-charged residues comprises the steps of obtaining a nucleotide sequence encoding the protein resulted from replacement of the residues, and expressing the nucleotide sequence with the recombinant host cell to obtain the protein resulted from replacement of the residues.

In the invention, the protein mixture can be obtained by separately cloning the different proteins into expression vectors, co-transfecting the different expression vectors into a host cell, and culturing the recombinant host cell to express the proteins; or by operably connecting and cloning the different proteins into one expression vector, and further transferring the expression vector into the host cell for culture.

In the invention, the process for obtaining the encoding nucleotide sequence based on the amino acid sequence resulted from replacement is well known in the art.

The second aspect of the invention relates to a mixture containing two or more proteins, wherein the proteins is in the form of a dimer which is formed by polymerization between monomer chains, and the two or more proteins contain the same domain, wherein part of residues of the two monomer chains in the same domain of one or more proteins are replaced with the opposite-charged amino acid(s), so that the monomer chains from the different proteins are unfavorable to forming a heterodimer due to the repulsive interaction between like charges, while the monomer chain from the same protein is more favorable to forming a homodimer due to the attractive interaction between opposite charges.

In an embodiment of the invention, the proteins are antibodies or fusion proteins comprising a part of the antibodies.

The mixture according to any one embodiment of the second aspect of the invention, the residues of at most one protein or antibody are not replaced. In an embodiment of the invention, the residues of one protein are not replaced and the residues of the other protein are replaced. In another embodiment of the invention, the residues of the two proteins are both replaced.

When the residues of multiple (two or more) proteins are replaced, at least one position of the replaced residues among different proteins are different, preferably, all the positions of the replaced residues among different proteins are different.

The mixture according to of any one embodiment of the second aspect of the invention, the same domain refers to CH3 domain of an antibody.

The mixture according to any one embodiment of the second aspect of the invention, the same domain refers to Fc region of an antibody.

The mixture according to any one embodiment of the second aspect of the invention, the antibodies are derived from mammals, such as human, mice or rats.

The mixture according to any one embodiment of the second aspect of the invention, the antibodies are selected from the group consisting of IgG (such as IgG1, IgG2, IgG3), IgA (such as IgA1, IgA2), IgE, IgD and IgM (such as IgM1, IgM2).

The mixture according to any one embodiment of the second aspect of the invention, wherein the part of the residues are interface residues between the same domains of the two monomer chains of the protein, preferably, the interface residues are the charged residues with paired positive and negative charges; and more preferably, one or more pairs (such as two pairs, three pairs or four pairs) of paired residues are replaced with the opposite-charged residues.

In an embodiment of the invention, the charged amino acid is selected from the group consisting of lysine (lys), arginine (Arg), histidine (His), aspartic acid (Asp) and glutamic acid (Glu).

In an embodiment of the invention, the same domain refers to Fc region or CH3 domain of the antibody, and the paired charged residues with paired positive and negative charges are selected from the group consisting of the following paired residues as shown in a)-h):

a) Glu (E) at position 356 of the first chain and Lys (K) at position 439 of the second chain;

b) Glu (E) at position 357 of the first chain and Lys (K) at position 370 of the second chain;

c) Lys (K) at position 370 of the first chain and Glu (E) at position 357 of the second chain;

d) Lys (K) at position 392 of the first chain and Asp (D) at position 399 of the second chain;

e) Asp (D) at position 399 of the first chain and Lys (K) at position 392 of the second chain;

f) Asp (D) at position 399 of the first chain and Lys (K) at position 409 of the second chain;

g) Lys (K) at position 409 of the first chain and Asp (D) at position 399 of the second chain; and h) Lys (K) at position 439 of the first chain and Glu (E) at position 356 of the second chain;

the positions of the above 8 pairs of residues are determined according to the EU numbering index of KABAT system for antibody.

In an embodiment of the invention, replacing the part of residues of the two monomer chains in the same domains of one or more proteins with the opposite-charged residues refers to one or any combination of the following situations:

(1) replacing Lys at position 392 with Asp, replacing Lys at position 409 with Asp and replacing Asp at position 399 with Lys for one protein;

(2) replacing Glu at position 356 with Lys and replacing Lys at position 439 with Glu for one protein;

(3) replacing Glu at position 357 with Lys and replacing Lys at position 370 with Glu for one protein;

(4) replacing Glu at position 357 with Lys, replacing Lys at position 370 with Glu, replacing Lys at position 392 with Asp, replacing Lys at position 409 with Asp and replacing Asp at position 399 with Lys for one protein;

(5) replacing Lys at position 392 with Asp and replacing Asp at position 399 with Lys for one protein;

(6) replacing Asp at position 399 with Lys and replacing Lys at position 409 with Asp for one protein;

(7) replacing Lys at position 392 with Asp, replacing Lys at position 409 with Asp and replacing Asp at position 399 with Lys for one protein; and simultaneously, replacing Glu at position 357 with Lys and replacing Lys at position 370 with Glu for the other protein; and (8) replacing Lys at position 392 with Asp, replacing Lys at position 409 with Asp and replacing Asp at position 399 with Lys for one protein; and simultaneously, replacing Glu at position 356 with Lys and replacing Lys at position 439 with Glu for the other protein.

In an embodiment of the invention, the paired charged residues with the paired positive and negative charges in a sequence as shown in SEQ ID NO: 2 are 8 pairs of residues as shown in a1)-h1):

a1) Glu (E) at position 161 of the first chain and Lys (K) at position 244 of the second chain;
b1) Glu (E) at position 162 of the first chain and Lys (K) at position 175 of the second chain;
c1) Lys (K) at position 175 of the first chain and Glu (E) at position 163 of the second chain;
d1) Lys (K) at position 197 of the first chain and Asp (D) at position 204 of the second chain;
e1) Asp (D) at position 204 of the first chain and Lys (K) at position 197 of the second chain;
f1) Asp (D) at position 204 of the first chain and Lys (K) at position 214 of the second chain;
g1) Lys (K) at position 214 of the first chain and Asp (D) at position 204 of the second chain;
h1) Lys (K) at position 244 of the first chain and Glu (E) at position 161 of the second chain.

In an embodiment of the invention, the paired charged residues with the paired positive and negative charges in the sequence as shown in SEQ ID NO: 4 are 8 pairs of residues as shown in a2)-h2):

a2) Glu (E) at position 399 of the first chain and Lys (K) at position 482 of the second chain;
b2) Glu (E) at position 400 of the first chain and Lys (K) at position 413 of the second chain;
c2) Lys (K) at position 413 of the first chain and Glu (E) at position 400 of the second chain;
d2) Lys (K) at position 435 of the first chain and Asp (D) at position 442 of the second chain;
e2) Asp (D) at position 442 of the first chain and Lys (K) at position 435 of the second chain;
f2) Asp (D) at position 442 of the first chain and Lys (K) at position 452 of the second chain;
g2) Lys (K) at position 452 of the first chain and Asp (D) at position 442 of the second chain;
h2) Lys (K) at position 482 of the first chain and Glu (E) at position 399 of the second chain.

The third aspect of the invention relates to the protein mixture obtained according to the method of any one embodiment of the first aspect of the invention.

Polypeptides containing CH3 domains form interaction interfaces due to interaction between residues and thus form dimers, therefore, in an embodiment of the invention, a method for obtaining a homodimer mixture is described, wherein the attractive interaction between two CH3 domains in a heterodimer can be reduced by modifying the residues on the interaction interfaces of CH3 domains through the repulsive effect of the charges, resulting in a mixture of homodimer. Generally speaking, on heterodimer's CH3-CH3 interface, the repulsive effect of the charges can be formed by modifying the related residues as charged residues. In some cases, when a certain amino acid with positive charges (lysine, arginine, histidine) on the interface is mutated to one with negative charges (aspartic acid, glutamic acid), the repulsive effect can be formed, and vise versa.

In an embodiment of the invention, upon interaction of the residues on CH3-CH3 interface, the interaction between the charged residues in the pairs is determined, any one or more of the residues are selected, and the effect of the selected residues on the formation of homodimers and heterodimers is analyzed, then the selected residues are mutated to charged residues, and the effect of mutated residues on the formation of homodimers and heterodimers after mutation is investigated, then the effects after and before the mutations are compared, and an appropriate mutation would result in the effect of strengthening the formation of homodimers and weakening the formation of heterodimers. Finally, reasonable mutations of the residues are selected to maximize the effect of strengthening the formation of homodimers and weakening the formation of heterodimers.

In a specific embodiment, the method described above is defined as follows: the paired charged residues in the CH3 domains of the homodimer proteins are mutated to the opposite-charged residues, so that homodimers can be formed between Fc of the two monomer chains, due to the interaction resulted from the attractive interaction of the paired opposite-charged residues, while heterodimers cannot be formed due to the repulsive interaction of like charges resulted from the interchange of the electric properties of the charges of the paired amino acids on one chain, and thus obtaining the Fc antibody or Fc-fusion protein mixture which only comprises the homodimers.

In the invention, the protein, also called polypeptide, contains more than 10 residues, preferably more than 50 residues and more preferably more than 100 residues. In an embodiment of the invention, the protein is an antibody or comprise a part of an antibody. In the specific embodiment of the invention, the protein is Fc fragment of IgG1. In another embodiment of the invention, the protein is a fusion protein of single-chain variable-fragment (ScFv) and Fc fragment of IgG1.

In the invention, the host cell is a cell suitable for expressing proteins or antibodies, such as a prokaryotic cell or a eukaryotic cell. One example for a prokaryotic cell is *E. coli*; the examples for a eukaryotic cell are a yeast cell or a mammalian cell; and the examples for a mammalian cell are a human epithelial cell (such as 293H), a Chinese hamster ovary cell (CHO) or a myeloma cell.

In the invention, the different protein contains the same domain. In an embodiment of the invention, the same domains refer to CH3 domains of antibodies or Fc regions of antibodies.

In the invention, the monomer chain, also called the single polypeptide, refers to one monomer or one subunit to form the dimer protein. In an embodiment of the invention, the two monomer chains forming the dimer are symmetric, namely the sequences of the two monomer chains are the same.

In the invention, replacing the residues refers to replacing the residues in the corresponding positions of the two monomer chains forming the dimer protein.

In the invention, the dimer refers to a combination formed by two subunits or two monomers during the formation of protein or nucleic acid, and the subunits or monomers can be combined by covalent bonds or non-covalent bonds; the homodimer means that the sequence of two subunits forming the dimer are the same; and the heterodimer means that the two subunits of the dimer are different.

In the invention, the domain refers to the region with specific structure and independent function in bio-macromolecules, particularly in proteins. In an embodiment of the invention, the domain refers to CH3 domain of an antibody or Fc region of an antibody.

In the invention, the interface residues refer to the residues which form contact interfaces between the domains. The interface residues consist of two or more residues.

In the invention, the one protein or the same protein refers to the protein expressed from of one nucleotide sequence, namely the protein formed as homodimer.

The protein or antibody mixture obtained using the method of the invention can be a mixture of two or more protein or antibody homodimers, preferably a mixture of two protein or antibody homodimers.

In an embodiment of the invention, the domain containing CH3 can be only CH3 domain, or human immunoglobulin Fc region containing CH3 domain. In general, the polypeptides of CH3 domains of human immunoglobulin Fc region are derived from wild-type human immunoglobulin Fc region. The wild-type human immunoglobulin Fc refers to an amino acid sequence that occurs within human population. Of course, Fc sequence may vary slightly among individuals. The human immunoglobulin Fc in the invention also contains fragments with several residue alterations as compared with the wild-type human immunoglobulin Fc sequence, such as alterations of some residues in Fc region, comprising some residues mutated at glycosylation sites or other mutations. The sequence of CH3 domain can be for example the sequence as shown in positions 148-252 of SEQ ID NO: 2. The sequence of Fc region can be for example the sequence as shown in positions 26-252 of SEQ ID NO: 2.

In the invention, the term "human immunoglobulin Fc" refers to human immunoglobulin fragment crystallizable, is the C-terminal part of a human immunoglobulin chain constant region, in particular the immunoglobulin heavy chain constant region. For example, the immunoglobulin Fc region may comprise the combination of two or more domains of CH2, CH3 and CH4 of heavy chains with an immunoglobulin hinge region. Herein, Fc region of IgG corresponds to the lower hinge region —CH2-CH3 domain (for IgG, CH2 and CH3 are also called Cγ2 and Cγ3 domains). In the background of human IgG1, according to EU indexes in Kabat system, the lower hinge region refers to positions 226-236, CH2 domain refers to positions 237-340, and CH3 domain refers to positions 341-447. According to the amino acid sequence of heavy chain constant region, immunoglobulins can be divided into different types. There are mainly five types of immunoglobulins: IgA, IgD, IgE, IgG and IgM, wherein some of the immunoglobulins can be further divided into sub-types (isotypes): such as IgG-1, IgG-2, IgG-3, IgG-4, IgA-1 and IgA-2. The similar domains of other IgG sub-types can be determined by comparing heavy chains or heavy chain fragments of the IgG sub-types with the amino acid sequence of heavy chain or heavy chain fragments of human IgG1. Selecting specific immunoglobulin Fc regions from specific immunoglobulin types and sub-types is within the scope of those skilled in the art. Because the residues interactive interface of immunoglobulin monomers are highly conserved between human and murine, the method of preparing a homodimer protein or antibody mixture by using the repulsive interaction of charges is also suitable for both human and murine IgA, IgD, IgE, IgG and IgM. The related method is also suitable for mutating the non-charged residues of CH3domains to the charged residues.

In the invention, the residues in Fc region are numbered according to the EU indexes for the immunoglobulin heavy chain (Kabat, et al., Sequences of Proteins of Immunological Interest, 5th Ed, Public Health Service, National Institutes of Health, Bethesda, Md. (1991), which is cited here for reference). The EU indexes of Kabat system refer to the EU residue numbering for human IgG1 antibody. The positions in the amino acid sequence of antibody Fc region are indicated with the EU indexes mentioned in Kabat, et al.

In the invention, the antibody prototypes for producing homodimer protein mixture can be antibodies, immunoglobulins, Fc fusion polypeptides, Fc conjugates (see FIG. 2), but the list is not intended for limiting.

In the invention, the homodimer proteins may be a homodimer protein of a polypeptide containing Fc regions, which include but are not limited to antibodies, Fc fusion proteins, Fc conjugates, Fc-derived polypeptides, isolated Fc and fragments thereof. Therefore, the homodimer protein may be a natural polypeptide, variants of the natural polypeptide, engineered forms of the natural polypeptides, synthetic polypeptides or polypeptides containing non-protein fragments. The engineered forms of the natural polypeptides are polypeptides which are not encoded by natural genes. For example, the engineered polypeptides can be chimeric antibodies or humanized antibodies.

In the invention, the homodimer mixture may be purified from the recombinant cells with a standard experimental technique. For example, when the homodimer protein comprises an Fc region, the protein may be purified using protein A. The purification methods include but are not limited to chromatographic methods such as size exclusion, ion exchange, affinity-based chromatography and ultrafiltration. The separation and purification methods of the homodimer mixture of the invention also include any appropriate combination of the above methods.

The invention further relates to an engineered monomer chain or an engineered single polypeptide for constituting the homodimer protein or antibody.

The invention further relates to a nucleic acid sequence encoding the engineered homodimer protein or antibody (or the monomer chain or the single polypeptide).

The invention further relates to a pharmaceutical composition comprising the engineered homodimer protein or antibody (or the monomer chain or the single polypeptide).

ADVANTAGES OF THE INVENTION

Due to the interaction between the same domains of different proteins (such as Fcs of antibodies), the formation of the homodimers and heterodimers is a dynamic and complex process, which involves the formation of stable homodimers due to the interaction of the interface residues of the homodimers, and the formation of stable heterodimers due to the interaction of the interface residues of the heterodimers, as well as the dynamic changes in the content of the heterodimers due to the existence of homodimers, and the dynamic changes in the content of the homodimers due to the existence of heterodimers. The invention provides a method for preparing a mixture of two or more proteins or antibodies with a single recombinant cell clone, which can increase the content of the homodimers of the proteins or antibodies and can reduce the content of other undesired products, such as the heterodimers. The experimental results show that the protein or antibody mixture obtained by the invention has pure components and desired stability. The protein or antibody mixture prepared by the invention can simultaneously act on different epitopes of the same target, or simultaneously inhibit the functions of different antigens, thereby providing a new method and routine for treatment of tumors and other diseases.

BRIEF DESCRIPTION OF THE DRAWINGS

FIG. 3 is alignment of human (a) and murine (b) IgG subtype sequences. In the figure, the alignment of CH3 of heavy chains is performed, wherein residues indicated with star (*) are the residues in CH3-CH3 interaction regions according to crystal structure of an human IgG1 Fc, and residues indicated with square frame represent preferable amino acid mutations for forming a homodimer mixture. It should be noticed that most of the charged residues in IgGs are highly conservative. (c) represents the comparison of CH3 sequences of other antibody subtypes (IgA, IgE, IdD and IgM). The stars (*) in (b) and (c) represent the residues in the CH3-CH3 interactive regions according to human IgG1.

FIG. 4 is a schematic diagram of the interaction of charges in wild-type and the interaction of charges in mutant, the latter hinders the formation of heterodimer and enhance the formation of homodimer. (a) In the case of wild type, the interaction of charges facilitate the formation of both heterodimer and homodimer. (b) In case of double mutations (D399K and K409D) inCH3 domain of Fc region of one chain, the heterodimer cannot be formed due to repulsive interaction of the charges and a homodimer mixture can be easily formed due to the attractive interaction of the charges.

SPECIFIC MODELS FOR CARRYING OUT THE INVENTION

Figure 1:
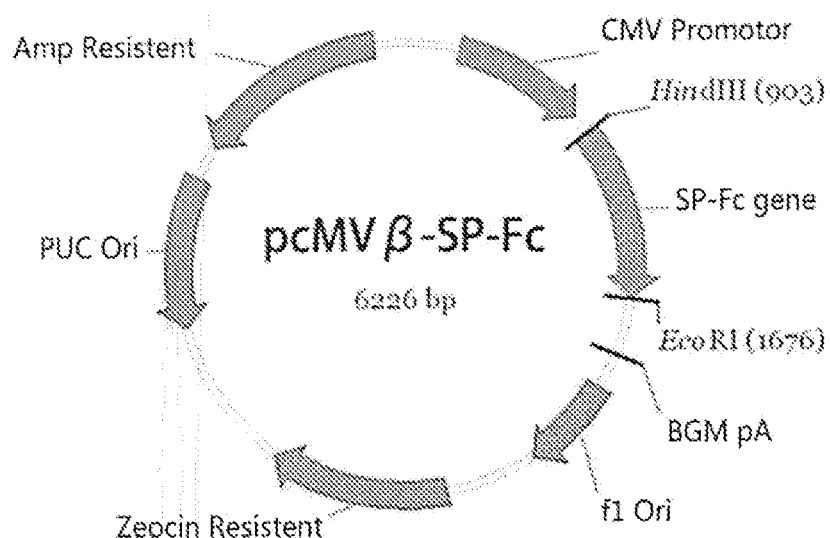
FIG. 1 is a schematic diagram of structure of a recombinant vector pcMVβ-SP-Fc.

The embodiments of the invention are illustrated in detail by referring to the examples, but those skilled in the art would understand that the following examples are merely for illustrating the invention and should not be deemed as restriction of the invention. The examples in which specific conditions are not given are performed according to conventional conditions or conditions suggested by manufacturers. The reagents or instruments for which manufacturers are not given are all conventional products commercially available.

Unless otherwise specified, the experimental methods used in the following examples are conventional methods.

Unless otherwise specified, materials, reagents and the like used in the following examples are commercially available.

EXAMPLE 1

Selection of Mutated Residues in CH3 Domain of Antibody Fc Fragments

1. Obtaining of Sequences and Structures

Crystal structures of 48 human IgG1 antibody containing Fc regions are obtained from a protein database (PDB, www.pdb.orq) and Fc fragments of the 48 antibodies were derived from 1DN2 (PDB number) upon a structure similarity searching algorithm (Reference: Yuzhen Ye and Adam Godzik. FATCAT: a web server for flexible structure comparison and structure similarity searching. Nucleic Acids Res., 2004, 32(Web Server issue): W582-585.).

2. Determination of Interface Residues

Interface amino acid prediction software CMA (URL: http://ligin.weizmann.acil/cma/) was used for screening and recognizing contact residues between CH3-CH3 in the antibodies (PDB number: 1 DN2) based on the distances of residues interaction. According to the contact rules of amino acid residues, the interface residues refer to those with the distances (from the heavy atoms of a side chain to the heavy atoms of any of residues of another chain) smaller than a limit. In this example, the distance limit was set as either 4.5 Å or 5.5 Å (See B. Erman, I. Bahar and R. L. Jernigan. Equilibrium states of rigid bodies with multiple interaction sites. Application to protein helices. J. Chem. Phys. 1997, 107:2046-2059.). The conservation of contact interfaces of residues of human and murine IgG subtype could be determined by multiple alignments of sequences in FIG. 3. Table 1 showed 34 interface residues of antibody 1DN2 identified by screening with the contact rules of residues (namely the distance between the residues is smaller than 4.5 Å), wherein the chain A and the chain B represented the first chain and the second chain of antibody 1 DN2, respectively. The positions of the following residues were designated by EU index of KABAT numbering system for antibody Fc.

TABLE 1

List of CH3—CH3 Interface Residues of Antibody 1DN2

| Contact amino acid in chain A | Contact amino acid in chain B |
|---|---|
| Gln347A | Lys360B |
| Val348A | Glu356B |
| Tyr349A | Ser354B, Glu356B, Glu357B, Lys360B |
| Thr350A | Ser354B, Glu356B |
| Leu351A | Leu351B, Pro352B, Pro353B, Ser354B, Thr366B |
| Pro352A | Leu351B, Pro352B |
| Pro353A | Leu351B |
| Ser354A | Tyr349B, Thr350B, Leu351B |
| Glu356A | Val348B, Tyr349B, Thr350B, Lys439B |
| Glu357A | Tyr349B, Leu368B, Lys370B |
| Lys360A | Gln347B, Tyr349B, Lys370B |
| Gln362A | Lys370B |
| Val363A | Lys370B |
| Ser364A | Leu368B, Lys370B, Tyr407B |
| Leu365A | Tyr407B |
| Thr366A | Leu351B, Leu368B, Tyr407B |
| Leu368A | Glu357B, Ser364B, Thr366B, Lys409B |
| Lys370A | Glu357B, Lys360B, Gln362B, Ser364B, Lys409B, Thr411B |

TABLE 1-continued

List of CH3—CH3 Interface Residues of Antibody 1DN2

| Contact amino acid in chain A | Contact amino acid in chain B |
|---|---|
| Asn390A | Ser400B |
| Lys392A | Val397B, Leu398B, Asp399B, Ser400B, Phe405B |
| Thr393A | Val397B |
| Thr394A | Thr394B, Val397B, Phe405B, Tyr407B |
| Pro395A | Pro395B, Val397B |
| Val397A | Lys392B, Thr393B, Thr394B, Pro395B |
| Leu398A | Lys392B |
| Asp399A | Lys392B, Lys409B, Thr411B |
| Ser400A | Asn390B, Lys392B |
| Phe405A | Lys392B, Thr394B, Tyr407B, Lys409B |
| Leu406A | Thr394B |
| Tyr407A | Thr366B, Thr394B, Phe405B, Tyr407B, Lys409B |
| Ser408A | Tyr407B |
| Lys409A | Leu368B, Lys370B, Asp399B, Phe405B, Tyr407B |
| Thr411A | Lys370B, Asp399B |
| Lys439A | Glu356B |

3. Searching for Paired Charged Residues

On the basis of the CH3-CH3 interface residues listed in Table 1, the paired charged residues were selected according to the charges of the residues, the results were shown in Table 2 and there were 8 pairs of charged residues.

TABLE 2

Paired Charged Residues of Antibody 1DN2

| Contact amino acid in chain A | Contact amino acid in chain B |
|---|---|
| Glu356A | Lys439B |
| Glu357A | Lys370B |
| Lys370A | Glu357B |
| Lys392A | Asp399B |
| Asp399A | Lys392B |
| Asp399A | Lys409B |
| Lys409A | Asp399B |
| Lys439A | Glu356B |

4. Mutation of Charged Residues

According to the results of Table 2, the two Fc chains of antibody 1DN2 are two symmetrical chains. Thus, for the paired residues of any chain, if the residue at a certain position of one chain is mutated to the residue with opposite charge, then the residue at the same position of the two chains of the antibody are both mutated, and for example, for the paired residues Glu356A-Lys439B, the two types of mutation are as follows:

1) the Glu356A is mutated to Lys356A or Arg356A, and/or the Lys439A is mutated to Glu439A or Asp439A; and 2) the Glu356B is mutated to Lys356B or Arg356B, and/or the Lys439B is mutated to Glu439B or Asp439B.

In this case, the opposite charges mean that the positive-charged residues (lysine (Lys, K) or arginine (Arg, R) or histidine (His, H)) are mutated to the negative-charged residues (aspartic acid (Asp, D) or glutamic acid (Glu, E)) or the negative-charged residues (aspartic acid or glutamic acid) are mutated to the positive-charged residues (lysine or arginine). The specific mutation positions are as shown in Table 3 and Table 4.

TABLE 3

Mutated Residues in chain A

| Amino acid in chain A | Charges of amino acid after mutation | Amino acid in chain A | Charges of amino acid after mutation |
|---|---|---|---|
| Glu356A | + | Lys439A | − |
| Glu357A | + | Lys370A | − |
| Lys392A | − | Asp399A | + |
| Asp399A | + | Lys409A | − |

Note:
+ represents positive charges and − represents negative charges.

TABLE 4

Mutated Residues in chain B

| Amino acid in chain B | Charges of amino acid after mutation | Amino acid in chain B | Charges of amino acid after mutation |
|---|---|---|---|
| Glu356B | + | Lys439B | − |
| Glu357B | + | Lys370B | − |
| Lys392B | − | Asp399B | + |
| Asp399B | + | Lys409B | − |

Note:
+ represents positive charges and − represents negative charges.

In addition, in more complicated cases, the operation can also be based on the method as above or the combinations of mutations of the paired residues described above. The method for modifying Fc (for preparation of Fc mixture) and preparing an antibody mixture according to the solution of the invention was not limited by double mutations of paired residues of the single-chain as mentioned above or any combination of the mutations.

EXAMPLE 2

Preparation of a Homodimer Protein Mixture by Modifying Residues in a CH3 Domain of an Antibody Fc Fragment 1. Construction of a Recombinant Vector pcMVβ-SP-Fc for Expressing a Fc Fragment of Human IgG1

According to the gene sequence of Fc fragment (hing-CH2-CH3) of human IgG1 in a gene database, a human Fc gene as shown in SEQ ID NO: 1, which contained at two terminals Hind III and EcoRI as recognition sequence and protective bases respectively (780 bp in length and named as SP-Fc), was obtained by artificial synthesis. The Fc gene was double digested with EcoRI and Hind III, and the resulted fragment was connected with the vector backbone of expression vector pcMVβ for mammalian cells (Invitrogen) which had been double digested with EcoRI and Hind III, and the recombinant vector pcMVβ-SP-Fc (the schematic diagram of its structure is as shown in FIG. 1) was obtained. It was proved upon sequencing that the recombinant vector pcMVβ-Fc was a vector wherein a DNA fragment as shown by the nucleotide sequence from the positions 16 to 771 in SEQ ID NO: 1 was inserted between EcoRI and Hind III sites of pcMVβ.

The amino acid sequence of Fc protein encoded by the nucleotide sequence of the positions 16 to 771 in SEQ ID NO: 1 is as follows (as shown in SEQ ID NO: 2):

(SEQ ID NO: 2)
METDTLLLWVLLLWVPGSTGGSGGGDKTHTCPPCPAPELLGGPSVFLF

PPKPKDTLMISRTPEVTCVVVDVSHENPEVKFNWYVDGVEVHNAKTKP

REEQYNSTYRVVSVLTVLHQDWLNGKEYKCKVSNKALPAPIEKTISKA

KGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNH

YTQKSLSLSPGK.

Figure 2:
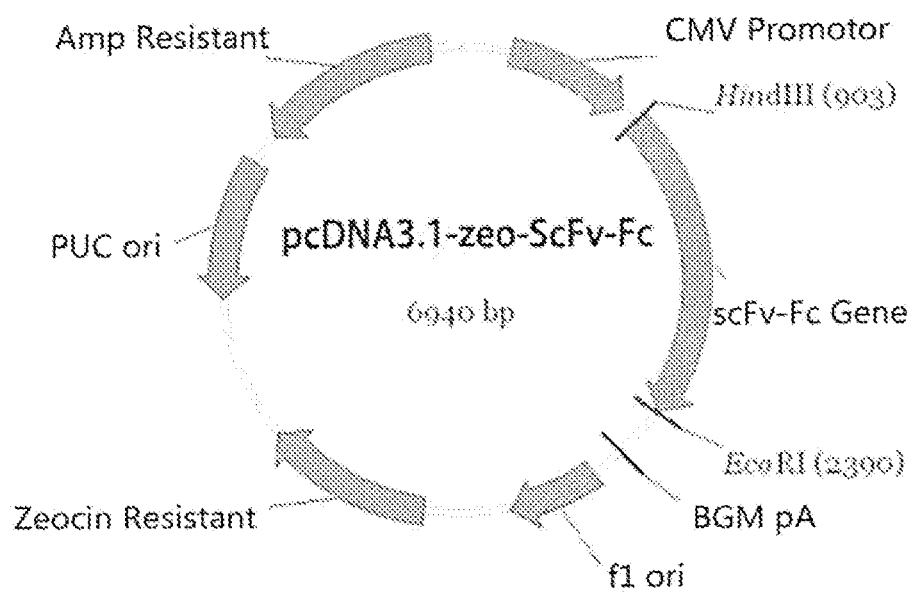
FIG. 2 is a schematic diagram of structure of a recombinant vector pcDNA3.1-zeo-ScFv-Fc.

2. Construction of a Recombinant Vector pcDNA3.1-zeo-ScFv-Fc for Expressing aScFv-Fc Fusion Protein The gene encoding ScFv-Fc fusion protein as shown in SEQ ID NO: 3 which contained Hind III and EcoRI at both terminals as recognition sequence and protective bases respectively was obtained by gene synthesis. The ORF encoding ScFv-Fc fusion protein was double digested with EcoRI and Hind III, and the resulted fragment was connected with the backbone of expression vector pcDNA3.1-zeo for mammalian cells (Invitrogen) which had been double digested with EcoRI and Hind III, and the recombinant vector pcDNA3.1-zeo-ScFv-Fc (the schematic diagram of the structure is as shown in FIG. 2) was obtained. It was proved upon sequencing that the recombinant vector pcDNA3.1-zeo-ScFv-Fc was a vector wherein the DNA fragment as shown by a nucleotide sequence from the positions 16 to 1488 in SEQ ID NO: 3 was inserted between the EcoRI and Hind III sites of pcDNA3.1-zeo with.

The amino acid sequence of ScFv-Fc fusion protein encoded by the nucleotide sequence of the positions 16 to 1488 in SEQ ID NO: 3 is as follows (as shown in SEQ ID NO: 4):

(SEQ ID NO: 4)
MGWSLILLFLVAVATRVLSEVQLLESGGGWQPGRSLRLSCIASGFTFS

SYPMTWVRQAPGKGLEWVASISYDGSYKYKADSMKGRLTISRDNSKNT

LYLEMNSLTAEDTAVYYCARTAFFNAYDFWGQGTLVTVSSASTKGPSV

GGGGSGGGGSEIVMTQSPATLSVSPGERATLSCRASQSVRSNLAWYQQ

KPGQAPRLLIYAASTRATGIPARFSGSGSGTEFTLTISSLQSEDFAVY

YCQQYNEWFRTSGQGTKVEIKRDKTHTCPPCPAPELLGGPSVFLFPPK

PKDTLMISRTPEVTCVVVDVSHENPEVKFNWYVDGVEVHNAKTKPREE

QYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQ

KSLSLSPGK.

The amino acid sequence of underlined parts in SEQ ID NO: 2 and SEQ ID NO: 4 are the same.

3. Preparation of a Engineered Recombinant Vector by Selecting Amino Acid Positions for Mutagenesis According to the residues to be mutated in Table 3 and Table 4 of Example 1, an overlapping PCR method was used for mutation and combined mutation of nucleotide sequences (SEQ ID NO: 1 and SEQ ID NO: 3) encoding scFV-Fc and Fc. As shown in the mutation combinations 1-8 in Table 5, 8 recombinant vectors pcDNA3.1-zeo-ScFv-Fc and pcMVβ-SP-Fc were obtained after engineering.

TABLE 5

Specific Mutations of Mutants and Positions Thereof

| Mutation combination | Mutated amino acid on ScFv-Fc protein | Position of mutated amino acid in SEQ ID NO: 4 | Mutated amino acid on Fc protein | Position of mutated amino acid in SEQ ID NO: 2 |
|---|---|---|---|---|
| 0 | WT | WT | WT | WT |
| 1 | NA | NA | K392D/K409D/D399K | K197D/K214D/D204K |
| 2 | NA | NA | E356K/K439E | E161K/K244E |
| 3 | NA | NA | E357K/K370E | E162K/K175E |
| 4 | NA | NA | E357K/K370E/K392D/K409D/D399K | E162K/K175E/K197D/K214D/D204K |
| 5 | E357K/K370E | E400K/K413E | K392D/K409D/D399K | K197D/K214D/D204K |
| 6 | E356K/K439E | E399K/K482E | K392D/K409D/D399K | K197D/K214D/D204K |
| 7 | NA | NA | K392D/D399K | K197D/D204K |
| 8 | NA | NA | D399K/K409D | D204K/K214D |

Note:
WT represents the wild type (without mutation),
NA represents no mutation is performed on the paired amino acid,
"/" represents the "and" relation,
365 in "E356K" represents the position of the mutated amino acid,
the letter E before 365 represents that the amino acid before mutation is E,
the letter K after 365 represents that the amino acid after mutation is K.
The same principle applies for other situations.

4. Detection of Transfected Cells and the Antibody Mixture

Figure 5:
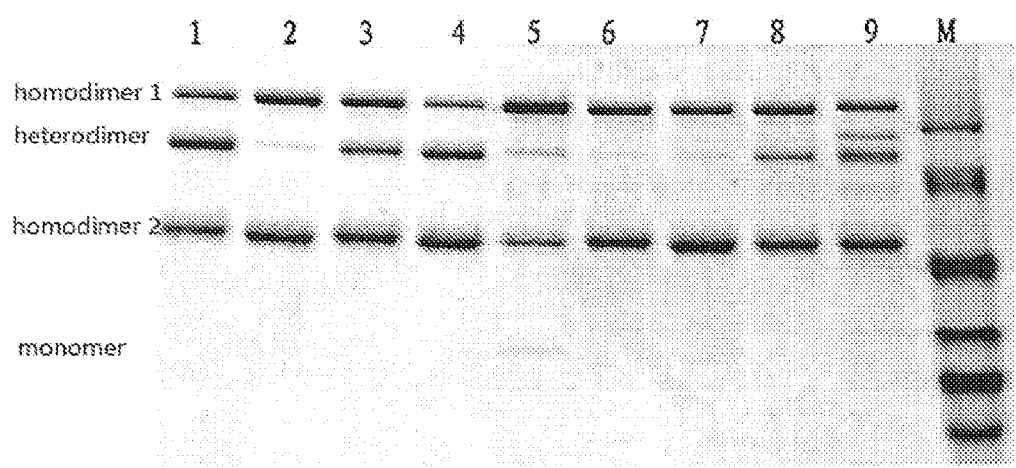
FIG. 5 is the results of electrophoresis analysis of the homodimers (ScFv-Fc/ScFv-Fc and Fc/Fc) and the heterodimer (ScFv-Fc/Fc), wherein lane M shows molecular weight markers (the top three fragments represent 104KD, 78KD and 50KD from top to bottom), and lanes 1-9 are mutation combinations 0-8 in Table 5, respectively.

The expression vectors harbor 8 mutation combinations in step 3 were separately transfected with PEI into suspension adapted 293H cells (ATCC CRL-1573), the co-transfection ratio of plasmids pcDNA3.1-zeo-ScFv-Fc to pcMVβ-SP-Fc was 1:1, and after 3-4 days, cell culture supernatant was collected. Immuno precipitation was performed with protein A agarose resin, and the content of the homodimer proteins or antibodies (ScFv-Fc/ScFv-Fc and Fc/Fc) and the heterodimer protein or antibody (ScFv-Fc/Fc) was detected by SDS-PAGE under non-reducing conditions. Gel-Pro professional image analysis software (Media Cybernetics company) was used for analyzing the proportion of the homodimer proteins or antibodies (ScFv-Fc/ScFv-Fc and Fc/Fc) and the heterodimer protein or antibody (ScFv-Fc/Fc). The results were as shown in FIG. 5 and Table 6. When the related mutation combination in Table 5 were introduced into ScFv-Fc, the proportion of the homodimers ScFv-Fc/ScFv-Fc and Fc/Fc was greatly increased, while the heterodimer (ScFv-Fc/Fc) was greatly reduced; and when three mutations K392D/K409D/D399K (mutation combination 2) or the mutation combinations 4, 5 or 6 were introduced into the Fc, the expressed proteins mainly existed in the forms of ScFv-Fc/ScFv-Fc and Fc/Fc homodimers (>96%), suggesting that the repulsive interaction of charges is crucial for enhancing the formation of the homodimers and hindering the formation of the heterodimer. It should be noticed that additional mutations (E357K/K370E or E356K/K439E) on ScFv-FC did not significantly increase the content of the homodimers, but increase the content of the heterodimer to a certain extent. In addition, when E357K/K370E/K392D/K409D/D399K (mutation combination 4) was introduced on Fc, the stability should be further investigated because of the appearance of Fc monomers (about 6%).

The method used for analyzing the composition of protein or antibody mixture is as follows: fusion protein ScFv-Fc has a greater molecular weight than Fc, therefore upon combination of ScFv-Fc and Fc, the homodimers (ScFv-Fc/ScFv-Fc and Fc/Fc) and the heterodimer (ScFv-Fc/Fc) would show different bands at positions in SDS-PAGE, the proportion of the homodimers and the heterodimer can be detected. The expression vectors of ScFv-Fc and Fc are co-transfected, and the homodimers (ScFv-Fc/ScFv-Fc and Fc/Fc) and the heterodimer (ScFv-Fc/Fc) can be visualized simultaneously.

only the scFV-Fc wild type is transfected) to perform accelerated stability study over 31 days under 45° C., and the SDS-PAGE analysis is performed on the day 0, 4, 8, 16, 21 and 31. Similarly, we selected antibody mixtures of the mutation combination 1 (mix 1), combination 6 (mix 2) and combination 0 (wild type, control) to perform CE-SDS (capillary electrophoresis) analysis on the day 0, 8, 21 and 31.

TABLE 6

Proportion of Homodimers and Heterodimer of Various Mutants on SDS-PAGE

| Mutation combination | Mutated amino acid on ScFv-Fc protein | Mutated amino acid on Fc protein | ScFV-FC homodimer | ScFV-FC heterodimer | Proportion of FC homodimer |
|---|---|---|---|---|---|
| 0 | WT | WT | 25.0 | 37.0 | 38.0 |
| 1 | NA | K392D/K409D/D399K | 44.5 | 4.2 | 51.3 |
| 2 | NA | E356K/K439E | 33.1 | 25.8 | 41.1 |
| 3 | NA | E357K/K370E | 19.9 | 32.7 | 47.5 |
| 4 | NA | E357K/K370E/K392D/K409D/D399K | 52.3 | 12.1 | 28.7 |
| 5 | E357K/K370E | K392D/K409D/D399K | 41.5 | 5.9 | 52.6 |
| 6 | E356K/K439E | K392D/K409D/D399K | 31.2 | 8.4 | 60.4 |
| 7 | NA | K392D/D399K | 36.4 | 18.9 | 44.7 |
| 8 | NA | D399K/K409D | 31.2 | 22.4 | 43.4 |

In order to investigate the influence of the co-transfection ratio of plasmids pcDNA3.1-zeo-ScFv-Fc to pcMVβ-SP-Fc on the ratios of the homodimers to the heterodimer, the plasmids pcDNA3.1-zeo-ScFv-Fc and pcMVβ-SP-Fc with the mutation combination 1 were co-transfected with PEI into 293H cells (ATCC CRL-1573) in suspension culture in the ratios of 4:1, 1:1 and 1:4, and after culturing for 3-4 days, the cell culture supernatant was collected. Immuno precipitation was performed with protein A agarose resin, and the content of the homodimer proteins or antibodies (ScFv-Fc/ScFv-Fc and Fc/Fc) and the heterodimer protein or antibody (ScFv-Fc/Fc) were detected by SDS-PAGE under non-reducing conditions. The results are shown in Table 7. It can be seen from the results that, by changing the co-transfection ratio of ScFV-Fc to Fc, the proportion of the different homodimers change, but the proportion of the heterodimer is always lower than 5%, suggesting that the mutation combination 1 can stably exclude the heterodimer.

TABLE 7

Influence of Different Co-transfection Ratios on Proportions of Homodimer and Heterodimers

| Co-transfection ratio of ScFV-Fc to Fc | ScFV-FC homodimer | ScFV-Fc/Fc heterodimer | Fc/Fc heterodimer |
|---|---|---|---|
| 4:1 | 71.0 | 3.8 | 25.2 |
| 1:1 | 44.1 | 4.3 | 51.6 |
| 1:4 | 23.8 | 4.1 | 72.1 |

According to the invention, by changing the co-transfection ratio of two plasmids comprising different Fc chains, the ratio of different homodimers can be adjusted to a certain extent, but the overall proportion of the homodimer as well as the proportion of the heterodimers cannot be significantly changed, indicating that the overall proportion of the homodimers keep stable while the co-transfection ratio of the plasmids is changed.

5. Accelerated Stability Study of the Antibody Mixtures

Figure 6:
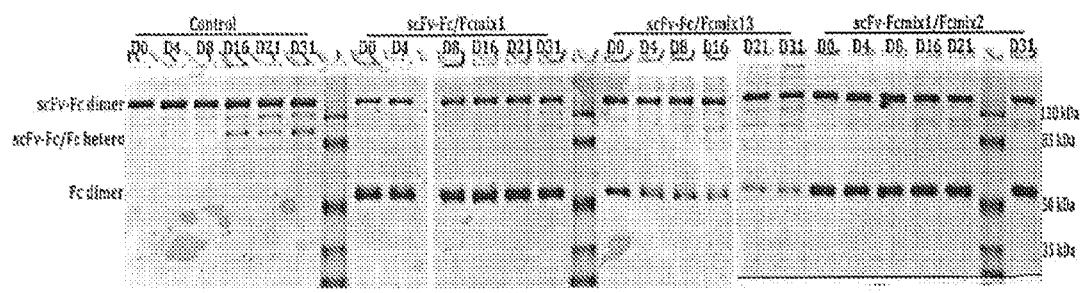
FIG. 6 is the result of an SDS-PAGE analysis in 31-day accelerated stability tests, wherein Control is wild type, scFv-Fc/Fc-mix1 is mutation combination 1, scFv-Fc/Fc-mix13 is mutation combination 4 and scFv-Fcmix1/Fc-mix2 is mutation combination 6.

Based on the results from the various mutation combinations on SDS-PAGE in step 4, we selected the antibody mixtures of mutation combination 1, 4, 6 and 0 (wild type, The 31-day accelerated stability SDS-PAGE results indicated that the mutation combination 1 and 6 showed very high stability, as the wild type (scFV/scFV homodimer, control) antibody mixtures. From Day 16, the ScFV-Fc/ScFV-Fc homodimers were partially degraded, while the Fc/Fc homodimers showed excellent stability till Day 31. Considering the instability of ScFV, it is considered that the antibody mixtures of mutation combination 1 and 6 had no differences in stability compared with wild-type Fc. It should be noticed that the antibody mixture produced by the mutation combination 4 showed relatively significant degradation with precipitation observed. It is speculated that with five mutations on single Fc chain (that is 10 mutations on Fc dimer), the structure was affected that causes the instability. The related results are as shown in FIG. 6.

Figure 7:
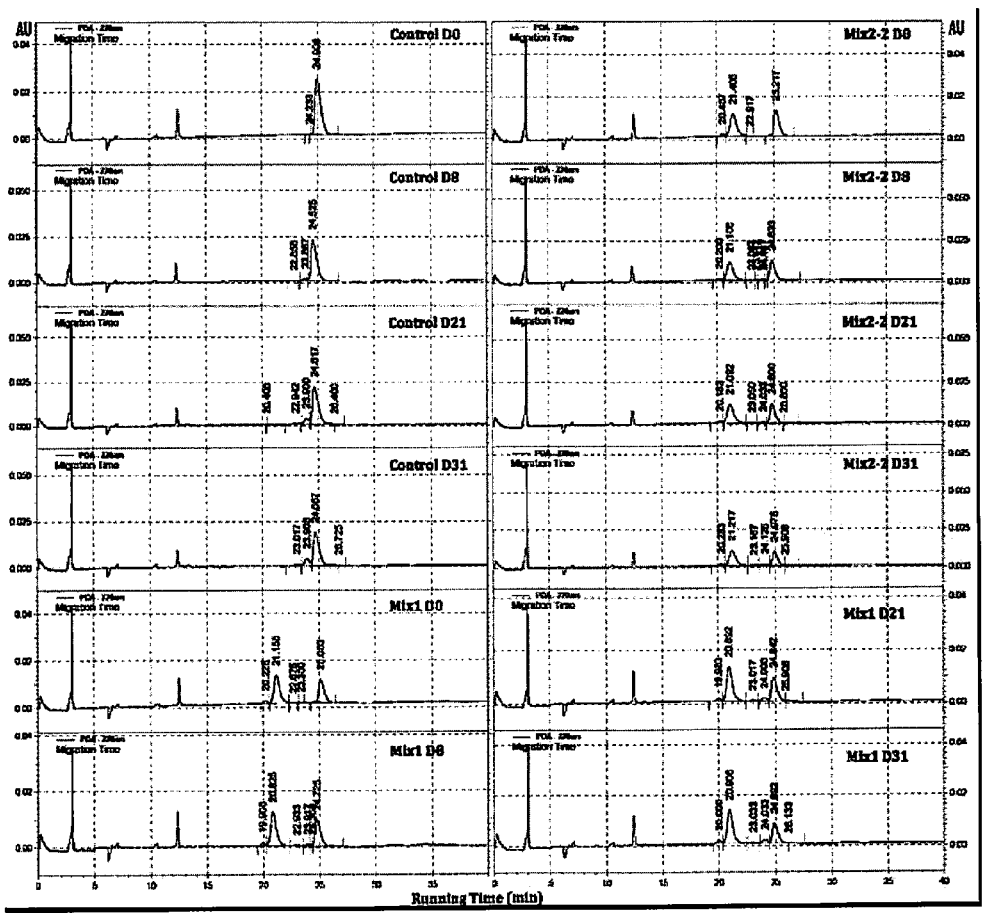
FIG. 7 is the result of a CE-SDS analysis in 31-day accelerated stability tests, wherein Control is wild type, Mix1 is mutation combination 1 and Mix2 is mutation combination 6.

In contrast to traditional SDS-PAGE, CE-SDS has advantages such as small loading amount of samples, capable of obtaining accurate molecular weight markers, in line detection with ultraviolet and the like, and quantitative analysis, etc. Thus this method can be used for measuring the degradation of the homodimer mixtures more accurately. It could be seen from FIG. 7 and Table 6 that the mutation combination 1 and 6 showed the same good stability as wild-type (control) antibody mixtures. A relatively obvious degradation peak of ScFV-Fc/ScFV-Fc homodimer samples appear from Day 16. The related results are consistent with the SDS-PAGE analysis of accelerated stability results.

TABLE 6

CE-SDS analysis of Antibody Mixtures under accelerated stability study

| Sample | | day 0 | day 8 | day 16 | day 31 |
|---|---|---|---|---|---|
| Control | main peak of scFv-Fc homodimer | 99.79% | 94.48% | 85.30% | 81.24% |
| | degradation peak of scFv-Fc homodimer | 0.21% | 5.51% | 13.72% | 18.19% |
| Mix1 | main peak of scFv-Fc homodimer | 42.88% | 40.02% | 35.20% | 32.75% |

TABLE 6-continued

CE-SDS analysis of Antibody Mixtures under accelerated stability study

| Sample | | day 0 | day 8 | day 16 | day 31 |
|---|---|---|---|---|---|
| | degradation peak of scFv-Fc homodimer | 0.36% | 4.77% | 7.85% | 8.27% |
| | main peak of Fc homodimer | 53.27% | 51.75% | 51.86% | 54.49% |
| | degradation peak of Fc homodimer | 3.49% | 3.46% | 3.67% | 3.63% |
| Mix2 | main peak of scFv-Fc homodimer | 47.01% | 44.21% | 40.33% | 35.93% |
| | degradation peak of scFv-Fc homodimer | 0.11% | 3.84% | 4.78% | 7.40% |
| | main peak of Fc homodimer | 49.42% | 48.43% | 49.51% | 50.9% |
| | degradation peak of Fc homodimer | 3.47% | 3.52% | 3.87% | 4.13% |

Although the specific models for carrying out the invention have been described in detail, those skilled in the art will understand these details can be modified and changed according to all teachings in the art, and these changes are within the protection scope of the invention. The whole scope of the invention is given by the attached claims and any equivalents thereof.

What is claimed is:

1. A method for obtaining a mixture containing two or more proteins by using a single recombinant cell clone, wherein the proteins are dimers formed by polymerization between two monomer chains, and the two or more proteins contain the same domain, wherein the method comprises the step of replacing one or more amino acid residues of the two monomer chains in the same domain of one or more proteins with opposite-charged residues, so that the monomer chains from different proteins are unfavorable to forming a heterodimer due to the repulsive interaction between like charges, while the monomer chain from the same protein is more favorable to forming a homodimer due to the attractive interaction between opposite charges;

wherein the same domain is a CH3 domain of an antibody or a Fc region of an antibody; and wherein an opposite-charged residue is introduced to replace:

1) Lys (K) at position 392, Lys (K) at position 409 and Asp (D) at position 399 of one protein;

2) Lys (K) at position 392, Lys (K) at position 409 and Asp (D) at position 399 of one protein, and Glu (E) at position 357 and Lys (K) at position 370 of another protein: or 3) Lys (K) at position 392, Lys (K) at position 409 and Asp (D) at position 399 of one protein, and Glu (E) at position 356 and Lys (K) at position 439 of another protein; and wherein: the positions of the residues are determined according to the EU numbering index of the KABAT system.

2. A mixture containing two or more proteins wherein the proteins are dimers formed by polymerization between two monomer chains, and the two or more proteins contain the same domain, wherein one or more amino acid residues of the two monomer chains in the same domain of one or more proteins are replaced with opposite-charged residues, so that the monomer chains from the different proteins are unfavorable to forming a heterodimer due to the repulsive interaction between like charges, while the monomer chain from the same protein is more favorable to forming a homodimer due to the attractive interaction between opposite charges, wherein the same domain is a CH3 domain of an antibody or a Fc region of an antibody;

wherein the following residues are replaced with an opposite-charged residue:

1) Lys (K) at position 392, Lys (K) at position 409 and Asp (D) at position 399 of one protein;

2) Lys (K) at position 392, Lys (K) at position 409 and Asp (D) at position 399 of one protein, and Glu (E) at position 357 and Lys (K) at position 370 of another protein; or 3) Lys (K) at position 392, Lys (K) at position 409 and Asp (D) at position 399 of one protein, and Glu (E) at position 356 and Lys (K) at position 439 of another protein; and wherein the positions of the residues are determined according to the EU numbering index of the KABAT system.

3. The mixture according to claim 2, wherein the antibody is derived from mammals.

4. The mixture according to claim 2, wherein the antibody is selected from the group consisting of IgG, IgA, IgE, IgD and IgM.

5. The mixture according to claim 2, wherein one or more amino acid residues of the two monomer chains in the same domain of one or more proteins being replaced with opposite-charged residues means that, for one protein, Lys at position 392 is replaced with Asp, Lys at position 409 is replaced with Asp and Asp at position 399 is replaced with Lys.

6. The protein mixture obtained by the method according to claim 1.

7. The method according to claim 1, wherein the antibody is derived from mammals.

8. The method according to claim 1, wherein the antibody is selected from the group consisting of IgG, IgA, IgE, IgD and IgM.

9. The method according to claim 1, wherein replacing one or more amino acid residues of the two monomer chains in the same domain of one or more proteins with opposite-charged residues means that, for one protein, Lys at position 392 is replaced with Asp, Lys at position 409 is replaced with Asp and Asp at position 399 is replaced with Lys.

10. The method according to claim 1, wherein the process of replacing one or more amino acid residues in the same domains with the opposite-charged residues comprises the steps of obtaining a nucleotide sequence encoding the protein resulted from the replacement of the residues, and expressing the nucleotide sequence with the recombinant host cell to obtain the protein resulted from the replacement of the residues.

11. A method of claim 1 for obtaining a mixture containing two or more proteins, wherein the proteins are antibodies.

12. The method according to claim 7, wherein the antibody is derived from humans.

13. The method according to claim 7, wherein the antibody is derived from mice and rats.

14. The method according to claim 8, wherein the antibody from the IgG group is selected from: IgG1, IgG2, and IgG3; the antibody from the IgA group is selected from: IgA1 and IgA2; and the antibody from the IgM group is selected from IgM1 and IgM2.

15. A mixture of claim 2 containing two or more proteins, wherein the proteins are antibodies.

16. The mixture according to claim 3, wherein the antibody is derived from humans.

17. The mixture according to claim 3, wherein the antibody is derived from mice or rats.

18. The mixture according to claim 4 wherein the antibody from the IgG group is selected from: IgG1, IgG2, and IgG3; the antibody from the IgA group is selected from:

IgA1 and IgA2, and the antibody from the IgM group is selected from: IgM1 and IgM2.

19. The method according to claim 1, wherein replacing one or more amino acid residues of the two monomer chains in the same domain of one or more proteins with the opposite-charged residues refers to:
   1) replacing Lys at position 392 with Asp, replacing Lys at position 409 with Asp and replacing Asp at position 399 with Lys for one protein;
   2) replacing Lys at position 392 with Asp, replacing Lys at position 409 with Asp and replacing Asp at position 399 with Lys for one protein; and simultaneously, replacing Glu at position 357 with Lys and replacing Lys at position 370 with Glu for another protein; or
   3) replacing Lys at position 392 with Asp, replacing Lys at position 409 with Asp and replacing Asp at position 399 with Lys for one protein; and simultaneously, replacing Glu at position 356 with Lys and replacing Lys at position 439 with Glu for another protein; and
   wherein the positions of the residues are determined according to the EU numbering index of the KABAT system.

20. The mixture according to claim 2, wherein one or more amino acid residues of the two monomer chains in the same domain of one or more proteins are replaced with the opposite-charged residues by:
   1) replacing Lys at position 392 with Asp, replacing Lys at position 409 with Asp and replacing Asp at position 399 with Lys for one protein;
   2) replacing Lys at position 392 with Asp, replacing Lys at position 409 with Asp and replacing Asp at position 399 with Lys for one protein; and simultaneously, replacing Glu at position 357 with Lys and replacing Lys at position 370 with Glu for another protein; or
   3) replacing Lys at position 392 with Asp, replacing Lys at position 409 with Asp and replacing Asp at position 399 with Lys for one protein; and simultaneously, replacing Glu at position 356 with Lys and replacing Lys at position 439 with Glu for another protein; and
   wherein the positions of the residues are determined according to the EU numbering index of the RABAT system.

* * * * *

SEQUENCE LISTING

```
<160> NUMBER OF SEQ ID NOS: 16

<210> SEQ ID NO 1
<211> LENGTH: 780
<212> TYPE: DNA
<213> ORGANISM: artificial sequence
<220> FEATURE:
<223> OTHER INFORMATION: synthetically created DNA

<400> SEQUENCE: 1
aagcttgccg ccaccatgga gaccgacacc ctgctgctgt gggtgctgct gctgtgggtg      60
cccggcagca ccggcggcag cggcggcggc gacaagaccc acacctgccc ccctgcccc     120 gcccccgagc tgctgggcgg ccccagcgtg ttcctgttcc cccccaagcc caaggacacc     180
ctgatgatca gcaggacccc cgaggtgacc tgcgtggtgg tggacgtgag ccacgaggac     240
cccgaggtga agttcaactg gtacgtggac ggcgtggagg tgcacaacgc caagaccaag     300
cccagggagg agcagtacaa cagcacctac agggtggtga gcgtgctgac cgtgctgcac     360
caggactggc tgaacggcaa ggagtacaag tgcaaggtga gcaacaaggc cctgcccgcc     420
cccatcgaga agaccatcag caaggccaag ggccagcccc gggagcccca ggtgtacacc     480 ctgccccca gcagggacga gctgaccaag aaccaggtga gcctgacctg cctggtgaag     540
ggcttctacc ccagcgacat cgccgtggag tgggagagca acggccagcc cgagaacaac     600
tacaagacca cccccccgt gctggacagc gacggcagct tcttcctgta cagcaagctg     660
accgtggaca gagcaggtg gcagcagggc aacgtgttca gctgcagcgt gatgcacgag     720
gccctgcaca accactacac ccagaagagc ctgagcctga gcccggcaa gtaagaattc     780

<210> SEQ ID NO 2
<211> LENGTH: 252
<212> TYPE: PRT
<213> ORGANISM: artificial sequence
<220> FEATURE:
<223> OTHER INFORMATION: synthetically created peptide

<400> SEQUENCE: 2

Met Glu Thr Asp Thr Leu Leu Leu Trp Val Leu Leu Leu Trp Val Pro
1               5                   10                  15

Gly Ser Thr Gly Gly Ser Gly Gly Gly Asp Lys Thr His Thr Cys Pro
            20                  25                  30

Pro Cys Pro Ala Pro Glu Leu Leu Gly Gly Pro Ser Val Phe Leu Phe
        35                  40                  45
```

```
Pro Pro Lys Pro Lys Asp Thr Leu Met Ile Ser Arg Thr Pro Glu Val
    50                  55                  60
Thr Cys Val Val Val Asp Val Ser His Glu Asn Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Asn Ser Thr Tyr Arg Val Val Ser Val Leu Thr
                100                 105                 110
Val Leu His Gln Asp Trp Leu Asn Gly Lys Glu Tyr Lys Cys Lys Val
            115                 120                 125
Ser Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Glu Glu Met Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
                180                 185                 190
Glu Asn Asn Tyr Lys Thr Thr Pro Pro Val Leu Asp Ser Asp Gly Ser
            195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys
                245                 250

<210> SEQ ID NO 3
<211> LENGTH: 1494
<212> TYPE: DNA
<213> ORGANISM: artificial sequence
<220> FEATURE:
<223> OTHER INFORMATION: synthetically created DNA

<400> SEQUENCE: 3
aagcttgccg ccaccatggg ctggagcctg atcctgctgt tcctggtggc cgtggccacc      60
agggtgctga gcgaggtgca gctgctggag agcggcggcg gcgtggtgca gcccggcagg     120
agcctgaggc tgagctgcat cgccagcggc ttcaccttca gcagctaccc catgacctgg     180
gtgaggcagg cccccggcaa gggcctggag tgggtggcca gcatcagcta cgacggcagc     240
tacaagtaca aggccgacag catgaagggc aggctgacca tcagcaggga caacagcaag     300
aacaccctgt acctggagat gaacagcctg accgccgagg acaccgccgt gtactactgc     360
gccaggaccg ccttcttcaa cgcctacgac ttctggggcc agggcaccct ggtgaccgtg     420
agcagcgcca gcaccaaggg ccccagcgtg gcggcggcg gcagcggcgg cggcggcagc     480
gagatcgtga tgacccagag ccccgccacc ctgagcgtga gccccggcga gagggccacc     540
ctgagctgca gggccagcca gagcgtgagg agcaacctgg cctggtacca gcagaagccc     600
ggccaggccc ccaggctgct gatctacgcc gccagcacca gggccaccgg catccccgcc     660
aggttcagcg gcagcggcag cggcaccgag ttccccctga ccatcagcag cctgcagagc     720
gaggacttcg ccgtgtacta ctgccagcag tacaacgagt ggttcaggac cagcggccag     780
ggcaccaagg tggagatcaa agggacaag acccacacct gcccccctg ccccgccccc     840
gagctgctgg gcggccccag cgtgttcctg ttcccccca agcccaagga caccctgatg     900
```

-continued

```
atcagcagga ccccccgaggt gacctgcgtg gtggtggacg tgagccacga ggaccccgag   960
gtgaagttca actggtacgt ggacggcgtg gaggtgcaca acgccaagac caagcccagg  1020
gaggagcagt acaacagcac ctacagggtg gtgagcgtgc tgaccgtgct gcaccaggac  1080
tggctgaacg gcaaggagta caagtgcaag gtgagcaaca aggccctgcc cgcccccatc  1140
gagaagacca tcagcaaggc caagggccag ccccgggagc cccaggtgta caccctgccc  1200
cccagcaggg acgagctgac caagaaccag gtgagcctga cctgcctggt gaagggcttc  1260
taccccagcg acatcgccgt ggagtgggag agcaacggcc agcccgagaa caactacaag  1320
accacccccc ccgtgctgga cagcgacggc agcttcttcc tgtacagcaa gctgaccgtg  1380
gacaagagca ggtggcagca gggcaacgtg ttcagctgca cgtgatgca cgaggccctg  1440 cacaaccact acacccagaa gagcctgagc ctgagccccg gcaagtaaga attc        1494
```

<210> SEQ ID NO 4
<211> LENGTH: 490
<212> TYPE: PRT
<213> ORGANISM: artificial sequence
<220> FEATURE:
<223> OTHER INFORMATION: synthetically created peptide

<400> SEQUENCE: 4

```
Met Gly Trp Ser Leu Ile Leu Leu Phe Leu Val Ala Val Ala Thr Arg
1               5                   10                  15

Val Leu Ser Glu Val Gln Leu Leu Glu Ser Gly Gly Gly Val Val Gln
                20                  25                  30

Pro Gly Arg Ser Leu Arg Leu Ser Cys Ile Ala Ser Gly Phe Thr Phe
            35                  40                  45

Ser Ser Tyr Pro Met Thr Trp Val Arg Gln Ala Pro Gly Lys Gly Leu
        50                  55                  60

Glu Trp Val Ala Ser Ile Ser Tyr Asp Gly Ser Tyr Lys Tyr Lys Ala
65                  70                  75                  80

Asp Ser Met Lys Gly Arg Leu Thr Ile Ser Arg Asp Asn Ser Lys Asn
                85                  90                  95

Thr Leu Tyr Leu Glu Met Asn Ser Leu Thr Ala Glu Asp Thr Ala Val
            100                 105                 110

Tyr Tyr Cys Ala Arg Thr Ala Phe Phe Asn Ala Tyr Asp Phe Trp Gly
        115                 120                 125

Gln Gly Thr Leu Val Thr Val Ser Ser Ala Ser Thr Lys Gly Pro Ser
    130                 135                 140

Val Gly Gly Gly Ser Gly Gly Gly Ser Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Arg Ser Asn Leu Ala Trp Tyr Gln
            180                 185                 190

Gln Lys Pro Gly Gln Ala Pro Arg Leu Leu Ile Tyr Ala Ala Ser Thr
        195                 200                 205

Arg Ala Thr Gly Ile Pro Ala Arg Phe Ser Gly Ser Gly Ser Gly Thr
    210                 215                 220

Glu Phe Thr Leu Thr Ile Ser Ser Leu Gln Ser Glu Asp Phe Ala Val
225                 230                 235                 240

Tyr Tyr Cys Gln Gln Tyr Asn Glu Trp Phe Arg Thr Ser Gly Gln Gly
                245                 250                 255

Thr Lys Val Glu Ile Lys Arg Asp Lys Thr His Thr Cys Pro Pro Cys
```

```
                    260                 265                 270
Pro Ala Pro Glu Leu Leu Gly Gly Pro Ser Val Phe Leu Phe Pro Pro
            275                 280                 285

Lys Pro Lys Asp Thr Leu Met Ile Ser Arg Thr Pro Glu Val Thr Cys
        290                 295                 300

Val Val Val Asp Val Ser His Glu Asn Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 5
<211> LENGTH: 109
<212> TYPE: PRT
<213> ORGANISM: homo sapiens

<400> SEQUENCE: 5

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 6
<211> LENGTH: 109
<212> TYPE: PRT
<213> ORGANISM: homo sapiens
```

<400> SEQUENCE: 6

```
Thr Lys Gly Gln Pro Arg Glu Pro Gln Val Tyr Thr Leu Pro Pro Ser
1               5                   10                  15
Arg Glu Glu Met Thr Lys Asn Gln Val Ser Leu Thr Cys Leu Val Lys
            20                  25                  30
Gly Phe Tyr Pro Ser Asp Ile Ser Val Glu Trp Glu Ser Asn Gly Gln
        35                  40                  45
Pro Glu Asn Asn Tyr Lys Thr Thr Pro Pro Met Leu Asp Ser Asp Gly
    50                  55                  60
Ser Phe Phe Leu Tyr Ser Lys Leu Thr Val Asp Lys Ser Arg Trp Gln
65                  70                  75                  80
Gln Gly Asn Val Phe Ser Cys Ser Val Met His Glu Ala Leu His Asn
                85                  90                  95
His Tyr Thr Gln Lys Ser Leu Ser Leu Ser Pro Gly Lys
            100                 105
```

<210> SEQ ID NO 7
<211> LENGTH: 109
<212> TYPE: PRT
<213> ORGANISM: homo sapiens

<400> SEQUENCE: 7

```
Thr Lys Gly Gln Pro Arg Glu Pro Gln Val Tyr Thr Leu Pro Pro Ser
1               5                   10                  15
Arg Glu Glu Met Thr Lys Asn Gln Val Ser Leu Thr Cys Leu Val Lys
            20                  25                  30
Gly Phe Tyr Pro Ser Asp Ile Ala Val Glu Trp Glu Ser Ser Gly Gln
        35                  40                  45
Pro Glu Asn Asn Tyr Asn Thr Thr Pro Pro Met Leu Asp Ser Asp Gly
    50                  55                  60
Ser Phe Phe Leu Tyr Ser Lys Leu Thr Val Asp Lys Ser Arg Trp Gln
65                  70                  75                  80
Gln Gly Asn Ile Phe Ser Cys Ser Val Met His Glu Ala Leu His Asn
                85                  90                  95
Arg Phe Thr Gln Lys Ser Leu Ser Leu Ser Pro Gly Lys
            100                 105
```

<210> SEQ ID NO 8
<211> LENGTH: 109
<212> TYPE: PRT
<213> ORGANISM: homo sapiens

<400> SEQUENCE: 8

```
Ala Lys Gly Gln Pro Arg Glu Pro Gln Val Tyr Thr Leu Pro Pro Ser
1               5                   10                  15
Gln Glu Glu Met Thr Lys Asn Gln Val Ser Leu Thr Cys Leu Val Lys
            20                  25                  30
Gly Phe Tyr Pro Ser Asp Ile Ala Val Glu Trp Glu Ser Asn Gly Gln
        35                  40                  45
Pro Glu Asn Asn Tyr Lys Thr Thr Pro Pro Val Leu Asp Ser Asp Gly
    50                  55                  60
Ser Phe Phe Leu Tyr Ser Arg Leu Thr Val Asp Lys Ser Arg Trp Gln
65                  70                  75                  80
Glu Gly Asn Val Phe Ser Cys Ser Val Met His Glu Ala Leu His Asn
                85                  90                  95
His Tyr Thr Gln Lys Ser Leu Ser Leu Ser Leu Gly Lys
```

<210> SEQ ID NO 9
<211> LENGTH: 106
<212> TYPE: PRT
<213> ORGANISM: mus musculus

<400> SEQUENCE: 9

Thr Lys Gly Arg Pro Lys Ala Pro Gln Val Tyr Thr Ile Pro Pro Pro
1               5                   10                  15

Lys Glu Gln Met Ala Lys Asp Lys Val Ser Leu Thr Cys Met Ile Thr
            20                  25                  30

Asp Phe Phe Pro Glu Asp Ile Thr Val Glu Trp Gln Trp Asn Gly Gln
        35                  40                  45

Pro Ala Glu Asn Tyr Lys Asn Thr Gln Pro Ile Met Asn Thr Asn Gly
    50                  55                  60

Ser Tyr Phe Val Tyr Ser Lys Leu Asn Val Gln Lys Ser Asn Trp Glu
65                  70                  75                  80

Ala Gly Asn Thr Phe Thr Cys Ser Val Leu His Glu Gly Leu His Asn
                85                  90                  95

His His Thr Glu Lys Ser Leu Ser His Ser
            100                 105

<210> SEQ ID NO 10
<211> LENGTH: 106
<212> TYPE: PRT
<213> ORGANISM: mus musculus

<400> SEQUENCE: 10

Pro Lys Gly Ser Val Arg Ala Pro Gln Val Tyr Val Leu Pro Pro Pro
1               5                   10                  15

Glu Glu Glu Met Thr Lys Lys Gln Val Thr Leu Thr Cys Met Val Thr
            20                  25                  30

Asp Phe Met Pro Glu Asp Ile Tyr Val Glu Trp Thr Asn Asn Gly Lys
        35                  40                  45

Thr Glu Leu Asn Tyr Lys Asn Thr Glu Pro Val Leu Asp Ser Asp Gly
    50                  55                  60

Ser Tyr Phe Met Tyr Ser Lys Leu Arg Val Glu Lys Lys Asn Trp Val
65                  70                  75                  80

Glu Arg Asn Ser Tyr Ser Cys Ser Val Val His Glu Gly Leu His Asn
                85                  90                  95

His His Thr Thr Lys Ser Phe Ser Arg Thr
            100                 105

<210> SEQ ID NO 11
<211> LENGTH: 106
<212> TYPE: PRT
<213> ORGANISM: mus musculus

<400> SEQUENCE: 11

Ile Lys Gly Leu Val Arg Ala Pro Gln Val Tyr Ile Leu Pro Pro Pro
1               5                   10                  15

Ala Glu Gln Leu Ser Arg Lys Asp Val Ser Leu Thr Cys Leu Val Val
            20                  25                  30

Gly Phe Asn Pro Gly Asp Ile Ser Val Glu Trp Thr Ser Asn Gly His
        35                  40                  45

Thr Glu Glu Asn Tyr Lys Asp Thr Ala Pro Val Leu Asp Ser Asp Gly
    50                  55                  60

Ser Tyr Phe Ile Tyr Ser Lys Leu Asn Met Lys Thr Ser Lys Trp Glu
 65                  70                  75                  80

Lys Thr Asp Ser Phe Ser Cys Asn Val Arg His Glu Gly Leu Lys Asn
                 85                  90                  95

Tyr Tyr Leu Lys Lys Thr Ile Ser Arg Ser
            100                 105

<210> SEQ ID NO 12
<211> LENGTH: 106
<212> TYPE: PRT
<213> ORGANISM: mus musculus

<400> SEQUENCE: 12

Pro Lys Gly Arg Ala Gln Thr Pro Gln Val Tyr Thr Ile Pro Pro Pro
 1               5                  10                  15

Arg Glu Gln Met Ser Lys Lys Val Ser Leu Thr Cys Leu Val Thr
                 20                  25                  30

Asn Phe Phe Ser Glu Ala Ile Ser Val Glu Trp Glu Arg Asn Gly Glu
             35                  40                  45

Leu Glu Gln Asp Tyr Lys Asn Thr Pro Pro Ile Leu Asp Ser Asp Gly
 50                  55                  60

Thr Tyr Phe Leu Tyr Ser Lys Leu Thr Val Asp Thr Asp Ser Trp Leu
 65                  70                  75                  80

Gln Gly Glu Ile Phe Thr Cys Ser Val Val His Glu Ala Leu His Asn
                 85                  90                  95

His His Thr Gln Lys Asn Leu Ser Arg Ser
            100                 105

<210> SEQ ID NO 13
<211> LENGTH: 114
<212> TYPE: PRT
<213> ORGANISM: homo sapiens

<400> SEQUENCE: 13

Ser Gly Asn Thr Phe Arg Pro Glu Val His Leu Leu Pro Pro Pro Ser
 1               5                  10                  15

Glu Glu Leu Ala Leu Asn Glu Leu Val Thr Leu Thr Cys Leu Ala Arg
                 20                  25                  30

Gly Phe Ser Pro Lys Asp Val Leu Val Arg Trp Leu Gln Gly Ser Gln
             35                  40                  45

Glu Leu Pro Arg Glu Lys Tyr Leu Thr Trp Ala Ser Arg Gln Glu Pro
 50                  55                  60

Ser Gln Gly Thr Thr Thr Phe Ala Val Thr Ser Ile Leu Arg Val Ala
 65                  70                  75                  80

Ala Glu Asp Trp Lys Lys Gly Asp Thr Phe Ser Cys Met Val Gly His
                 85                  90                  95

Glu Ala Leu Pro Leu Ala Phe Thr Gln Lys Thr Ile Asp Arg Met Ala
            100                 105                 110

Gly Lys

<210> SEQ ID NO 14
<211> LENGTH: 112
<212> TYPE: PRT
<213> ORGANISM: homo sapiens

<400> SEQUENCE: 14

Thr Ser Gly Pro Arg Ala Ala Pro Glu Val Tyr Ala Phe Ala Thr Pro

```
                 1               5                  10                 15
              Glu Trp Pro Gly Ser Arg Asp Lys Arg Thr Leu Ala Cys Leu Ile Gln
                                20                  25                 30

Asn Phe Met Pro Glu Asp Ile Ser Val Gln Trp Leu His Asn Glu Val
                                35                  40                 45

Gln Leu Pro Asp Ala Arg His Ser Thr Thr Gln Pro Arg Lys Thr Lys
                                50                  55                 60

Gly Ser Gly Phe Phe Val Phe Ser Arg Leu Glu Val Thr Arg Ala Glu
               65                70                  75                 80

Trp Glu Gln Lys Asp Glu Phe Ile Cys Arg Ala Val His Glu Ala Ala
                                85                  90                 95

Ser Pro Ser Gln Thr Val Gln Arg Ala Val Ser Val Asn Pro Gly Lys
                                100                 105                110

<210> SEQ ID NO 15
<211> LENGTH: 114
<212> TYPE: PRT
<213> ORGANISM: homo sapiens

<400> SEQUENCE: 15

Arg Glu Pro Ala Ala Gln Ala Pro Val Lys Leu Ser Leu Asn Leu Leu
1               5                   10                  15

Ala Ser Ser Asp Pro Pro Glu Ala Ala Ser Trp Leu Leu Cys Glu Val
                20                  25                  30

Ser Gly Phe Ser Pro Pro Asn Ile Leu Leu Met Trp Leu Glu Asp Gln
                35                  40                  45

Arg Glu Val Asn Thr Ser Gly Phe Ala Pro Ala Arg Pro Pro Pro Gln
                50                  55                  60

Pro Gly Ser Thr Thr Phe Trp Ala Trp Ser Val Leu Arg Val Pro Ala
65              70                  75                  80

Pro Pro Ser Pro Gln Pro Ala Thr Tyr Thr Cys Val Val Ser His Glu
                85                  90                  95

Asp Ser Arg Thr Leu Leu Asn Ala Ser Arg Ser Leu Glu Val Ser Tyr
                100                 105                 110

Val Thr

<210> SEQ ID NO 16
<211> LENGTH: 115
<212> TYPE: PRT
<213> ORGANISM: homo sapiens

<400> SEQUENCE: 16

Pro Lys Gly Val Ala Leu His Arg Pro Asp Val Tyr Leu Leu Pro Pro
1               5                   10                  15

Ala Arg Glu Gln Leu Asn Leu Arg Glu Ser Ala Thr Ile Thr Cys Leu
                20                  25                  30

Val Thr Gly Phe Ser Pro Ala Asp Val Phe Val Gln Trp Met Gln Arg
                35                  40                  45

Gly Gln Pro Leu Ser Pro Glu Lys Tyr Val Thr Ser Ala Pro Met Pro
                50                  55                  60

Glu Pro Gln Ala Pro Gly Arg Tyr Phe Ala His Ser Ile Leu Thr Val
65              70                  75                  80

Ser Glu Glu Glu Trp Asn Thr Gly Glu Thr Tyr Thr Cys Val Val Ala
                85                  90                  95
```

His Glu Ala Leu Pro Asn Arg Val Thr Glu Arg Thr Val Asp Lys Ser
            100                 105                 110
Thr Gly Lys
        115